United States Patent [19]
Kohno

[11] Patent Number: 5,602,639
[45] Date of Patent: Feb. 11, 1997

[54] SURFACE-CONDITION INSPECTION METHOD AND APPARATUS INCLUDING A PLURALITY OF DETECTING ELEMENTS LOCATED SUBSTANTIALLY AT A PUPIL PLANE OF A DETECTION OPTICAL SYSTEM

[75] Inventor: Michio Kohno, Tokyo, Japan

[73] Assignee: Canon Kabushiki Kaisha, Tokyo, Japan

[21] Appl. No.: 505,782

[22] Filed: Jul. 21, 1995

Related U.S. Application Data

[63] Continuation of Ser. No. 85,989, Jul. 6, 1993, abandoned.

[30] Foreign Application Priority Data

Jul. 8, 1992 [JP] Japan .................. 4-204495

[51] Int. Cl.$^6$ ........................................... G01N 21/88
[52] U.S. Cl. ........................................... 356/237
[58] Field of Search ........................... 356/237, 239

[56] References Cited

U.S. PATENT DOCUMENTS

| | | | |
|---|---|---|---|
| 3,879,131 | 4/1975 | Cuthbert et al. ............... | 356/71 |
| 4,460,273 | 7/1984 | Koizumi et al. ............... | 356/237 |
| 4,669,885 | 6/1987 | Ina ............................... | 356/443 |
| 4,795,911 | 1/1989 | Kohno et al. ................. | 250/572 |
| 4,831,274 | 5/1989 | Kohno et al. ................. | 250/563 |
| 4,886,974 | 12/1989 | Ina ............................... | 250/561 |
| 4,886,975 | 12/1989 | Murakami et al. ........... | 250/572 |
| 4,999,511 | 3/1991 | Kohno ........................... | 250/572 |
| 5,017,798 | 5/1991 | Murakami et al. ........... | 250/572 |
| 5,105,092 | 4/1992 | Natsubori et al. ............ | 250/572 |
| 5,162,867 | 11/1992 | Kohno ........................... | 356/237 |
| 5,363,187 | 11/1994 | Hagiwara et al. ............ | 356/237 |

FOREIGN PATENT DOCUMENTS 59-61762 4/1984 Japan.

*Primary Examiner*—Vincent P. McGraw
*Attorney, Agent, or Firm*—Fitzpatrick, Cella, Harper & Scinto

[57] ABSTRACT

A method and an apparatus for inspecting surface conditions of an object, on which a pattern is formed, by detecting scattered light generated by the surface of the object using a detection optical system. The method includes the steps of illuminating the surface of the object, providing first and second photodetectors on a pupil plane of the detection optical system, generating a first signal corresponding to the sum of the outputs of the first and second photodetectors, and a second signal corresponding to the difference between the outputs of the first and second photodetectors, and comparing the first signal with a first threshold value and the second signal with a second threshold value to obtain the logical product of the results of the comparisons for inspecting the surface of the object. The apparatus includes a detection optical system for detecting scattered light generated by the object illuminated by an illuminating device, first and second photodetectors provided at the pupil plane of the detection optical system, a device for comparing a signal corresponding to the sum of outputs of the first and second photodetectors with a first threshold value, and for comparing a signal corresponding to the difference between the outputs of the first and second photodetectors with a second threshold value, and a device for detecting the logical product of the results of the comparison by the comparison device.

15 Claims, 12 Drawing Sheets

FIG.9
| SIGNAL/ CALCULATION  STATE | VL | VR | θA $(V_L+V_R \geq V_A)$ | θC $\left|\frac{V_L-V_R}{V_L+V_R}\right| \leq R_C$ | θJ θA⊗θC |
|---|---|---|---|---|---|
| (a) NO FOREIGN PARTICLE | 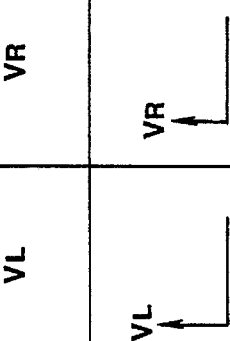 | 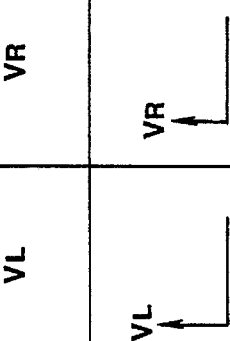 | θA 0 | 1 | 0 |
| (b) FOREIGN PARTICLE PRESENT | 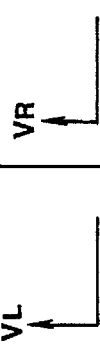 | 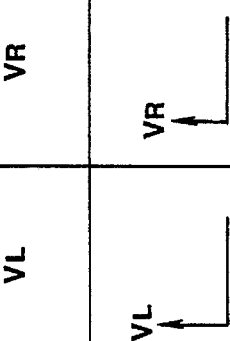 | θA 1 ⟵ VA | 1 | 1 |
| (c) CIRCUIT PATTERN 1 | 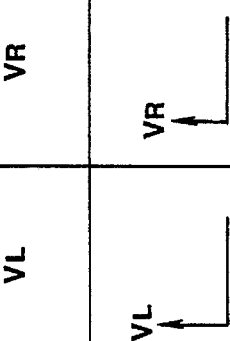 | 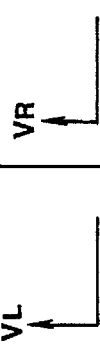 | θA 1 ⟵ VA | 0 | 0 |
| (d) CIRCUIT PATTERN 2 | 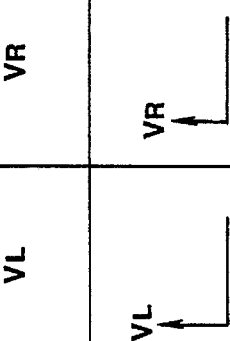 | 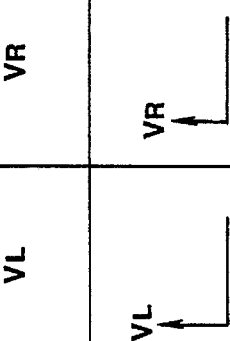 | θA 1 ⟵ VA | 0 | 0 |
| (e) CIRCUIT PATTERN 1 + FOREIGN PARTICLE PRESENT | 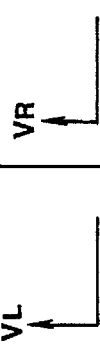 | 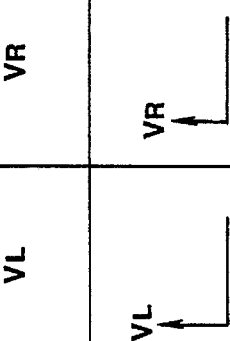 | θA 1 ⟵ VA | 1 | 1 |

SURFACE-CONDITION INSPECTION METHOD AND APPARATUS INCLUDING A PLURALITY OF DETECTING ELEMENTS LOCATED SUBSTANTIALLY AT A PUPIL PLANE OF A DETECTION OPTICAL SYSTEM

This application is a continuation of prior application Ser. No. 08/085,989 filed Jul. 6, 1993, now abandoned.

BACKGROUND OF THE INVENTION

1. Field of the Invention

This invention relates to a surface-condition inspection method and apparatus for inspecting conditions of a surface to be inspected, and more particularly, to a surface-condition inspection method and apparatus for discriminating the presence of defects or foreign particles on a reticle (photomask) used when manufacturing devices, such as semiconductor memories, liquid-crystal displays, magnetic heads or the like, or on a pellicle for protecting the reticle from foreign particles.

2. Description of the Related Art

In general, in the IC (integrated circuit) production process, circuit patterns formed on a substrate, such as a reticle, a photomask or the like, are transferred onto the surface of a wafer coated with a resist using a printing apparatus (e.g., a stepper or a mask aligner).

If foreign matter, such as pattern defects, dust particles or the like, is present on the surface of the substrate at the time of circuit pattern transfer, the foreign matter is also transferred, causing a decrease in the yield of the IC production.

In particular, when circuit patterns are printed onto the surface of a wafer by a step-and-repeat method using a reticle, if even one harmful foreign matter particle is present on the surface of the reticle and is printed onto the entire surface of the wafer, a great decrease in the yield of the IC production is caused.

Accordingly, the ability to detect the presence of foreign matter on a substrate in the IC production process is indispensable, and various kinds of inspection methods have been proposed for that purpose. In general, a method which utilizes the property that foreign matter isotropically scatters light has been used.

FIG. 1 is a diagram showing a schematic configuration of a principal part of a conventional surface-condition inspection apparatus.

In FIG. 1, light beam 1a emitted from laser 1 is incident upon beam expander 3 via pinhole plate 2. Expander 3 transforms the incident light beam 1a into a parallel light beam while increasing the beam's diameter, and the resultant light beam is incident upon polygonal mirror 4. After being reflected by polygonal mirror 4, light beam 1a is condensed onto reticle 6 by scanning lens 5. By rotating polygonal mirror 4, light beam 1a scans the surface of reticle 6 in a direction orthogonal to the plane of FIG. 1. Reticle 6 moves in the direction of two-headed arrow $S_1$ in synchronization with the scanning by the polygonal mirror 4. The entire surface of reticle 6 is thereby subjected to optical scanning.

If light beam 1a hits foreign matter, such as a pattern defect, a dust particle or the like, on the surface of reticle 6, scattered light is generated from the foreign matter. Light-receiving lens 7 of detection system BD condenses back-scattered light from the foreign matter.

The object field of light-receiving lens 7 includes the beam scanning line on reticle 6. The amount of light received by light-receiving lens 7 is limited by aperture stop 8 which defines the entrance pupil of the lens 7. Scattered light passing through aperture stop 8 is condensed onto the surface of field stop 10, and imaging lens 9 images reticle 6 on the surface of field stop 10. Field stop 10 has a slit-like opening, and has a function of blocking flare light and the like other than scattered light from the foreign matter, passing only scattered light from the beam scanning line, and guiding the light to light-receiving unit 12 via condenser lens 11. The scattered light from the foreign matter is detected by light receiving unit 12.

FIG. 2 is a diagram illustrating the directional property of circuit patterns on the surface of a reticle in an actual production process. Typical conventional circuit patterns mainly comprise pattern A, pattern B and pattern C whose directions with respect to the x axis are 90 degrees, 0 degree and 45 degrees, respectively. The apparatus shown in FIG. 1 receives a greater amount of diffracted light from pattern A than from the other patterns.

FIG. 3 shows a portion of the optical path of the apparatus of FIG. 1 when pattern A is formed on the surface of the reticle 6. In FIG. 3, to ease understanding of the paraxial relationship between the light-projecting system and the light-receiving system, the light-projecting system and the light-receiving system are illustrated on a straight line.

FIG. 4 illustrates a state in which pattern-diffracted light $S_{PO}$, though weak, appears on the surface of aperture stop 8 of detection system BD as a one-dimensional point sequence. The diameter $\phi_s$ of one spot of the pattern-diffracted light in the direction of the incident cross section (incident plane) depends on the line width and the pitch of a repeated pattern within the diameter of the inspection beam 19 when the beam 19 stands still, the wavelength of the inspection beam 19, and the focal length fd of light-receiving lens 7. On the other hand, the diameter $\phi_m$ of the one spot of the pattern-diffracted light in the scanning direction of the inspection beam 19 is determined by the product of the opening angle of the incident beam (i.e., the numerical aperture NAj of the light projecting system) and the focal length fd of light receiving lens 7.

Accordingly, when pattern A is present at central portion $P_O$ of the scanning line on the reticle 6, the pattern-diffracted light $S_{PO}$ can be blocked by providing light-blocking plate 13 as shown in FIG. 5 in front of aperture stop 8.

However, the following problems arise when the aperture of aperture stop 8 is partly limited by light-blocking plate 13.

That is, when inspection is performed in a state in which the reticle 6 has rotated by an error amount within the horizontal plane because of a mechanical positioning error, pattern-diffracted light $S_{PO}$ laterally deviates on the surface of aperture stop 8 by an amount determined by the product of the error and the focal length fd. As a result, the pattern-diffracted light passes through light-blocking plate 13, and is erroneously detected by light-receiving unit 12.

When a circuit pattern is disposed at a portion around the beam scanning line (portion $P_L$ in FIG. 3), pattern-diffracted light $S_{PL}$ on aperture stop 8 laterally deviates from the central portion. In general, this occurs when accuracy in the alignment of the pupils of the light projecting system and the light-receiving system is insufficient. In primary approximation, such lateral deviation does not occur if the reflecting point $P_R$ of polygonal mirror 4 and the central point $P_f$ of aperture stop 8 are in a conjugate relationship, and pattern-diffracted light $S_{PL}$ coincides with pattern-diffracted light $S_{PO}$ on the stop. This corresponds to a case in which the pupils are in alignment.

Actually, however, an adjustment for maintaining such a relationship requires accuracy, and a residual component usually remains. For example, as is apparent from FIG. 3, if point $P_f'$ is conjugate to point $P_R$, pattern-diffracted light $S_{PL}$ laterally deviates on the surface of aperture stop 8, and passes through light-blocking plate 13.

Even though point $P_f'$ is present at an ideal paraxial position, the diffracted light in some cases passes through light-blocking plate 13 due to the aberration of light-receiving lens 7. Strictly speaking, the reflecting point itself of the polygonal mirror laterally deviates in accordance with the rotation of the mirror. This lateral deviation corresponds to deviation on light-blocking plate 3. This is one of the factors which causes difficulty in adjustment.

In accordance with an increase in the degree of integration of semiconductor chips, circuit patterns having directions other than 0 degree, 90 degrees and 45 degrees have been used. For example, a circuit pattern D shown in FIG. 2 slightly rotates by an angle θ with respect to circuit pattern A. As shown in FIG. 17, diffracted light $S_{PO}$ generated by such a circuit pattern appears accompanied by lateral deviation and rotation on aperture stop 8.

If the size of light-blocking plate 13 is increased in order to overcome the above-described problems, the amount of blocking of scattered light from foreign matter also increases, causing a decrease in the S/N ratio.

SUMMARY OF THE INVENTION

The present invention has been made in consideration of the above-described problems.

It is an object of the present invention to provide a surface-condition inspection method and apparatus which can exactly perform inspection of a surface to be inspected.

The surface-condition inspection method of the present invention is characterized in a method for inspecting conditions of a surface of an object (e.g., a reticle, a photomask, a wafer or the like) on which a pattern is formed by detecting scattered light generated by the surface of the object using a detection optical system. The method includes illuminating the surface of the object, providing first and second photodetectors on a pupil plane of the detection optical system, generating a first signal corresponding to the sum of outputs of the first and second photodetectors and, a second signal corresponding to the difference between the outputs of the first and second photodetectors, and comparing the first signal with a first threshold value and the second signal with a second threshold value to obtain a logical product of the result of the comparisons for inspecting surface conditions of the object.

The surface-condition inspection apparatus of the present invention is characterized in an apparatus for detecting conditions of a surface of an object (e.g., a reticle, a photomask, a wafer or the like), on which a pattern is formed. The apparatus includes means for illuminating the object, a detection optical system, having a pupil plane at a position off an optical path of regularly-reflected light and an optical path of directly-advancing light generated when illuminating the object, for detecting scattered light generated by the object illuminated by the illuminating means, first and second photodetectors provided at the pupil plane of the detection optical system for detecting scattered light from the surface of the object, comparison means for comparing a signal corresponding to the sum of outputs of the first and second photodetectors with a first threshold value, and for comparing a signal corresponding to the difference between the outputs of the first and second photodetectors with a second threshold value, and means for detecting a logical product of results of the comparison by the comparison means.

The first and second photodetectors of the present invention are placed at the position of the pupil plane, that is, an aperture stop for determining the pupil plane, or at a position conjugate to that position. Preferably, a member for blocking diffracted light generated by the pattern on the object and incident upon the detection optical system is provided in front of the photodetectors placed at the above-described position. According to the above-described method and apparatus of the present invention, accuracy in inspection can be improved when discriminating the presence of a defect or foreign particle on a reticle (photomask) used when manufacturing devices, such as semiconductor memories, liquid-crystal displays, solid-state image pickup devices, magnetic heads or the like, or a pellicle for protecting the reticle from foreign particles.

Accordingly, the present invention can provide a device manufacturing method and an exposure apparatus comprising steps and means, respectively, for exactly determining whether or not a reticle (photomask) or a reticle having a pellicle for protecting the reticle from foreign particles used when producing devices, such as semiconductor memories, liquid-crystal displays, solid-state image pickup devices, magnetic heads or the like, can be used.

The present invention utilizes the fact that, when a circuit pattern and foreign matter (dust paticles, pattern defects and the like) coexist on a reticle, pattern-diffracted light from the circuit pattern has a very localized spatial distribution which depends on the line width of the circuit pattern, the opening angle (numerical aperture NA) of the inspection beam, the diameter of the inspection beam, the focal length of a light-receiving lens, and the like, while scattered light from foreign matter has a relatively uniform spatial distribution. This tendency is more pronounced if the inspected region is limited within a minute space.

Accordingly, in one aspect of the present invention, a detection optical system is provided at a portion separated from the directly-advancing light where the intensity of pattern-diffracted light is weak. At the same time, an aperture stop for defining the pupil plane of the system is provided so that the opening angle of the received light beam has the greatest value allowed from design (more specifically, greater than the open angle of the incident light beam) in order to maximize the amount of scattered light from foreign matter.

The scattered light incident upon the pupil plane of the detection optical system is sensed by fractional sensors or a light-sensing unit, comprising a plurality of photosensors, provided at that position to detect the accumulated amount of light beams and the comparative amount of light beams. In the case of diffracted light from the pattern, differences between the amounts of light detected by the photosensors have large values, since the distribution of the light is localized, and even though the accumulated amount of light has a large value. On the other hand, scattered light from foreign matter is deemed to have a uniform distribution within a small limited region like the pupilary plane of the detection optical system, and differences between the amounts of light detected by the photodetectors have a smaller value. By utilizing this property, foreign matter on the surface of a reticle is detected while discriminating it from a circuit pattern with a high detection resolution.

In another aspect of the present invention, the detection optical system includes an aperture stop for defining the pupil plane and the first and second photodetectors are provided at one of a plane of the aperture stop and a conjugate image thereof.

In still another aspect of the present invention, the first and second photodetectors are provided symmetrically with respect to a plane including an optical axis of the detection optical system and orthogonal to the surface to be inspected.

BRIEF DESCRIPTION OF THE DRAWINGS

FIG. 9 is an explanatory diagram illustrating the manner of discrimination between foreign matter and a circuit pattern by signal processing system 102 of the apparatus shown in FIG. 6;

Like components have been indicated by like reference numerals throughout the views.

DESCRIPTION OF THE PREFERRED EMBODIMENTS

Figure 6:
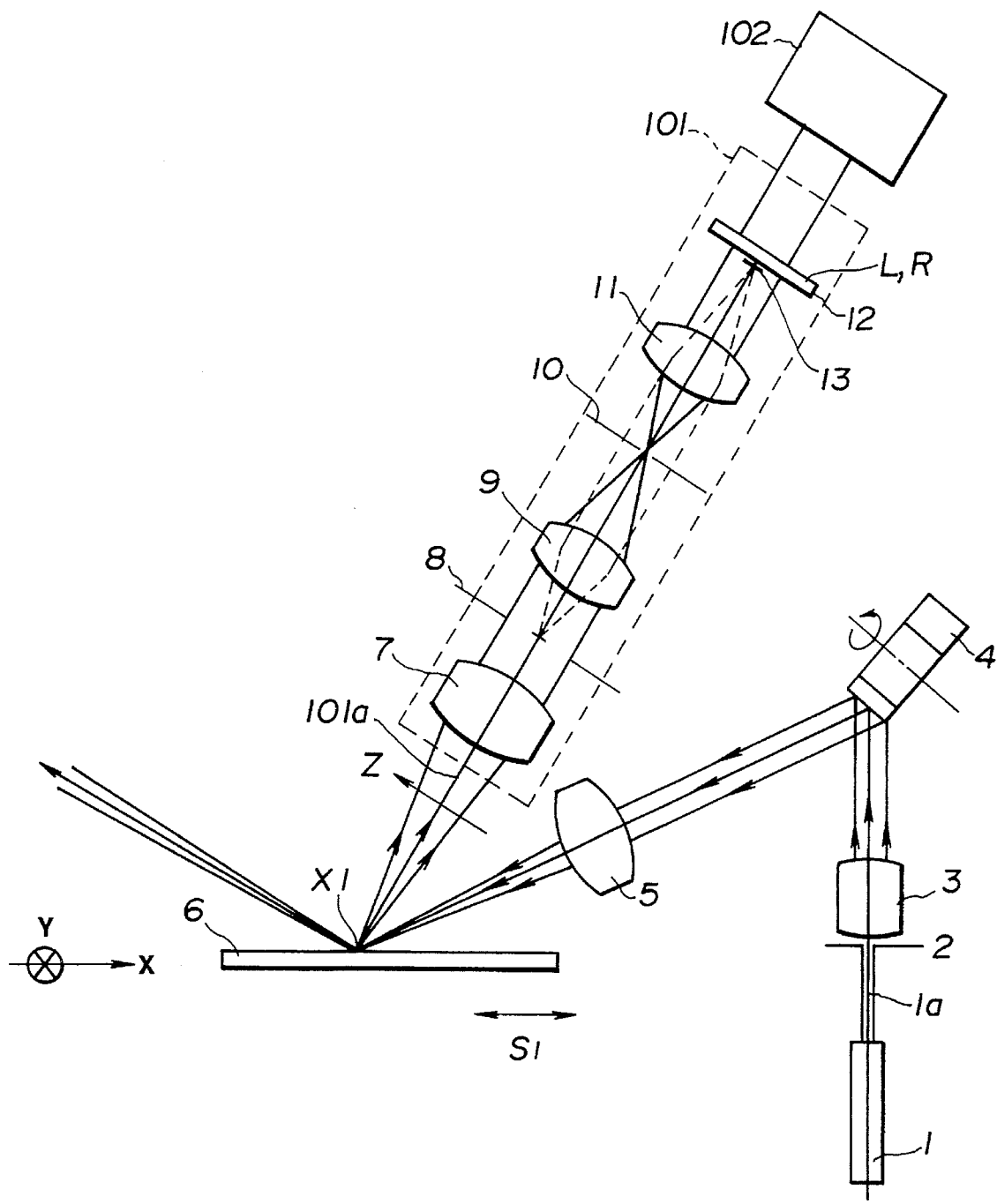
FIG. 6 is a diagram showing the schematic configuration of a foreign-matter inspection apparatus according to a first embodiment of the present invention.

FIG. 6 is a diagram showing the schematic configuration of a principal portion of an apparatus according to a first embodiment of the present invention. FIGS. 2, 7(A)–7(C) and 8 are explanatory diagrams, each illustrating a portion of FIG. 6. The apparatus of the present embodiment is used by being mounted in a projection exposure apparatus for device production, or independently.

In FIG. 6, light beam $1a$ emitted from laser 1, serving as light-source means, is incident upon beam expander 3 via pinhole plate 2. Expander 3 transforms the incident light beam $1a$ into a parallel light beam while increasing the beam's diameter, and the resultant light beam is incident upon polygonal mirror 4. After being reflected by polygonal mirror 4, light beam $1a$ is condensed onto the surface of reticle 6 to be inspected, on which a circuit pattern is formed, by scanning lens 5. By the rotation of polygonal mirror 4, light beam $1a$ scans the surface of reticle 6 in a direction orthogonal to the plane of FIG. 6. Reticle 6 is moved by a driving unit (not shown) in the direction of two-headed arrow $S_1$ within the plane of FIG. 6 in synchronization with the scanning by the polygonal mirror 4. The entire surface of reticle 6 is thereby subjected to optical scanning. If light beam $1a$ hits foreign matter X1, such as a pattern defect, a dust particle or the like, on the surface of reticle 6, scattered light is generated from the foreign matter X1.

Detection optical system system 101 receives scattered light from foreign matter X1 on the surface of reticle 6. Detection optical system 101 is disposed so that its optical axis $101a$ is situated at a portion other than the outgoing direction of regularly reflected light (directly-advancing light) of light beam $1a$ with respect to reticle 6.

Signal processing system 102 detects foreign matter X1 on the surface of reticle 6 while discriminating it from the circuit pattern using a signal from detection optical system 101 in a manner to be described later.

Next, a description will be provided of respective components of detection optical system 101 of the present embodiment.

Light-receiving lens 7 condenses scattered light from foreign matter X1, and guides the light to aperture stop 8 for defining the pupil of optical system 101. The field of view of light-receiving lens 7 includes beam scanning line $S_a$ (see FIG. 2) on reticle 6. Aperture stop 8 limits the amount of received light. With scattered light passing through aperture stop 8, the reticle 6 is imaged onto the plane of field stop 10 by imaging lens 9. Field stop 10 has a slit-like aperture parallel to beam scanning line $S_a$. Field stop 10 passes only scattered light from the portion of beam scanning line $S_a$, and guides the scattered light to light-sensing unit 12 via condenser lens 11. Aperture stop 8 is substantially conjugate to light-sensing unit 12 via imaging lens 9 and condenser lens 11. Light-sensing unit 12 comprises fractional sensors or a plurality of photosensors, and is provided at the pupilary plane of optical system 101.

Light-sensing unit 12 of the present embodiment provides two photosensors L and R symmetrically with respect to a plane including the optical axis (the same as optical axis $101a$ of detection optical system 101) of light-receiving lens 7, and orthogonal to reticle 6 as seen from the x direction. A plurality of photomultipliers, photodiodes, position sensors, CCD's (charge-coupled devices) or the like, can be used for photosensing unit 12. The essential point is to provide two light-sensing regions at opposite sides with respect to the optical axis. Light-blocking plate 13 is provided in front of photosensing unit 12 which is substantially conjugate to aperture stop 8.

In a modification of the present embodiment, light-blocking plate 13 and photosensing unit 12 are provided at the position of aperture stop 8, that is, the pupil plane of the optical system. In this case, components 9, 10 and 11 become unnecessary.

Figures 7A, 7B, 7C:
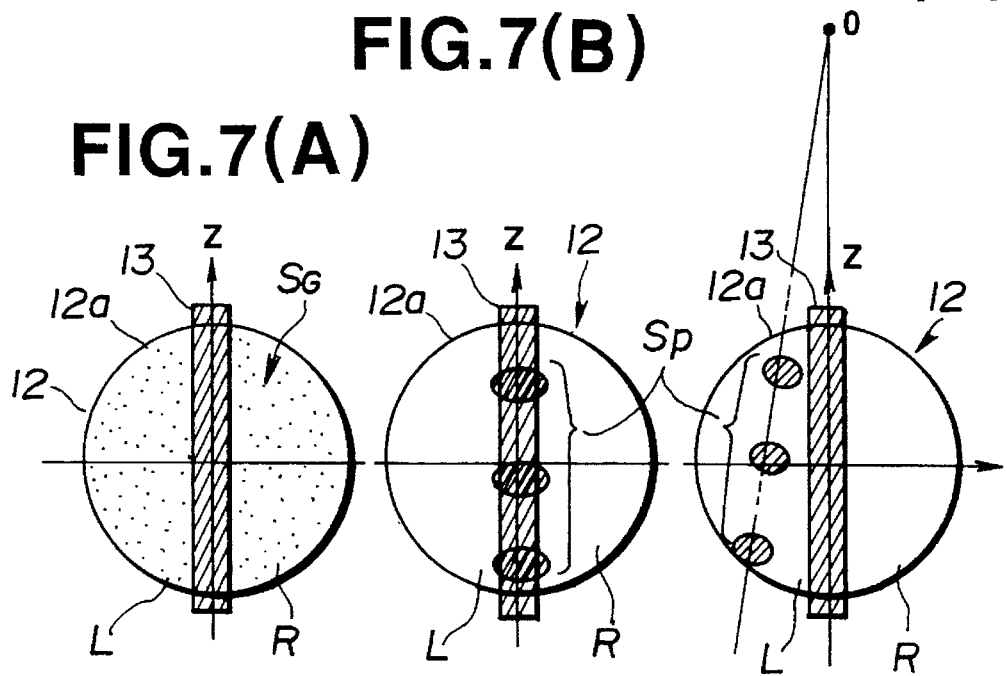
FIGS. 7(A)–7(C) are diagrams illustrating distributions of scattered light and diffracted light on photosensing unit 12 of the apparatus shown in FIG. 6.
Figure 3:
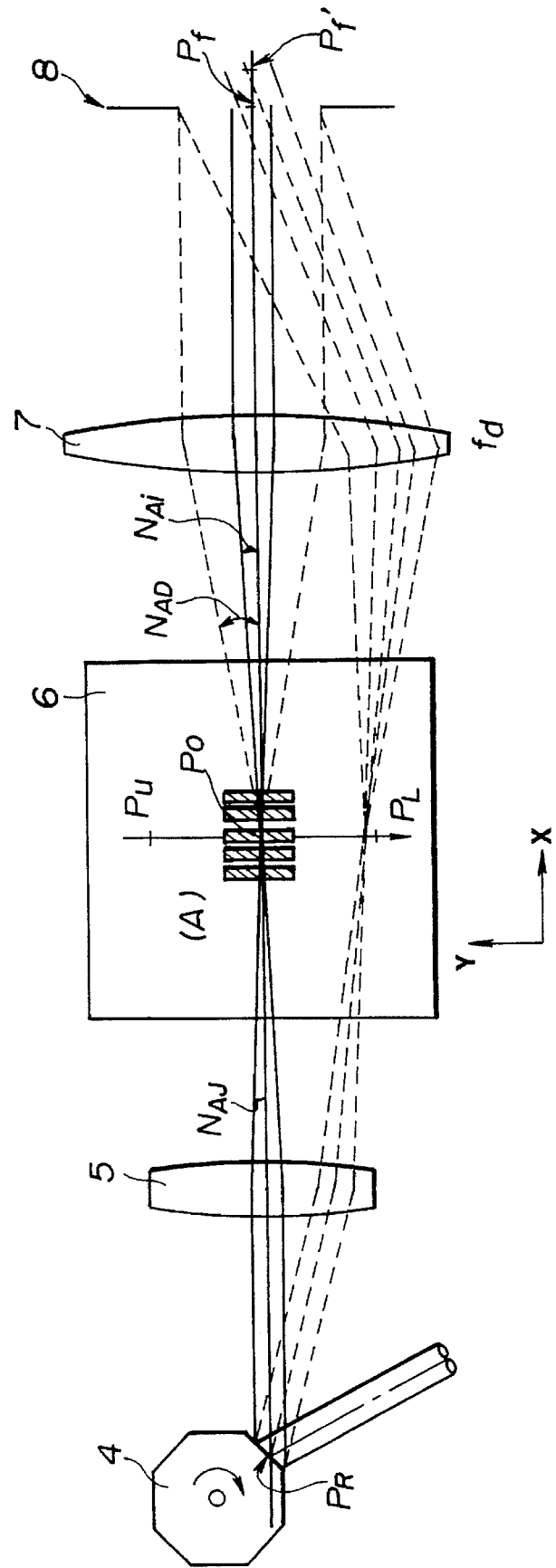
FIG. 3 is a view illustrating the optical path of the apparatus shown in FIG. 1.
Figure 4:
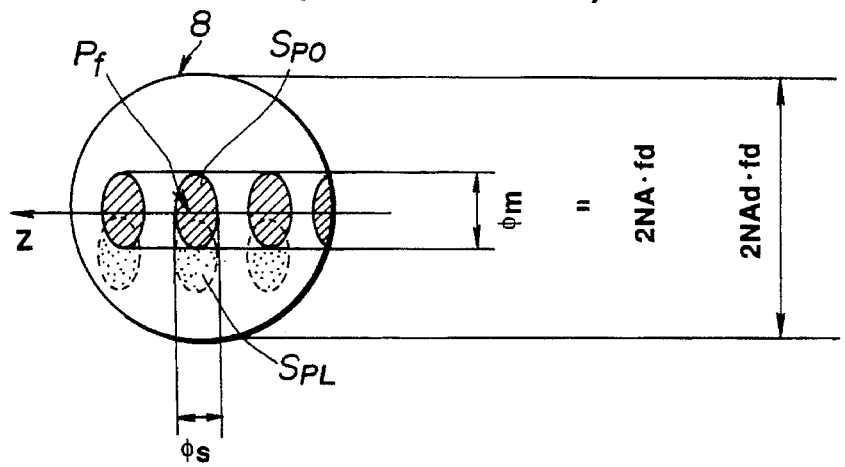
FIG. 4 is a diagram illustrating a distribution of diffracted light at the position of the aperture stop shown in FIG. 1.
Figure 5:
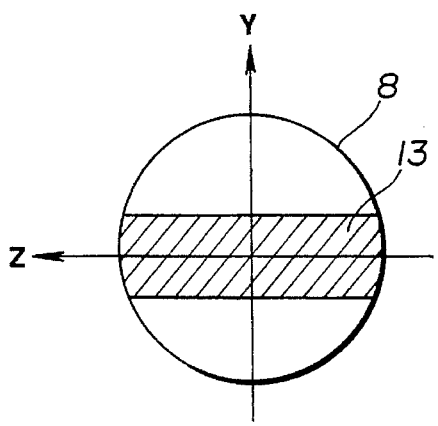
FIG. 5 is a diagram showing a light-blocking plate.
Figure 17:
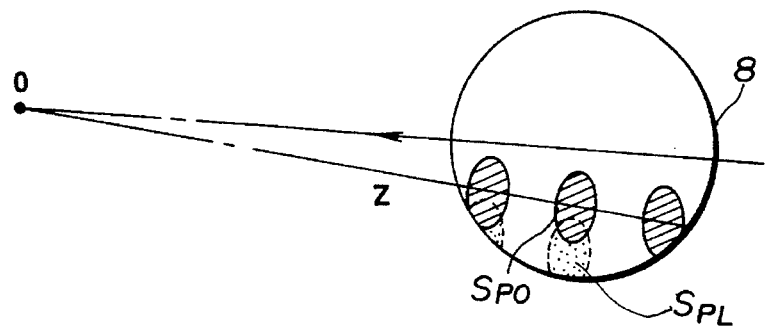
FIG. 17 is a diagram illustrating a distribution of diffracted light from pattern D shown in FIG. 2 at the position of the aperture stop shown in FIG. 1.

FIGS. 7(A), 7(B) and 7(C) illustrate the positional relationship between the two photosensors L and R of photosensing unit 12 and light-blocking plate 13, as well as scattered light $S_G$ and pattern-diffracted light $S_P$. FIG. 7(A) illustrates a state in which scattered light $S_G$ from foreign matter X1 on the surface of reticle 6 is incident upon the light receiving surface of the two photosensors L and R of photosensing unit 12 while being uniformly dispersed. At that time, the difference between signal outputs from the two photosensors L and R equals 0.

Figure 1:
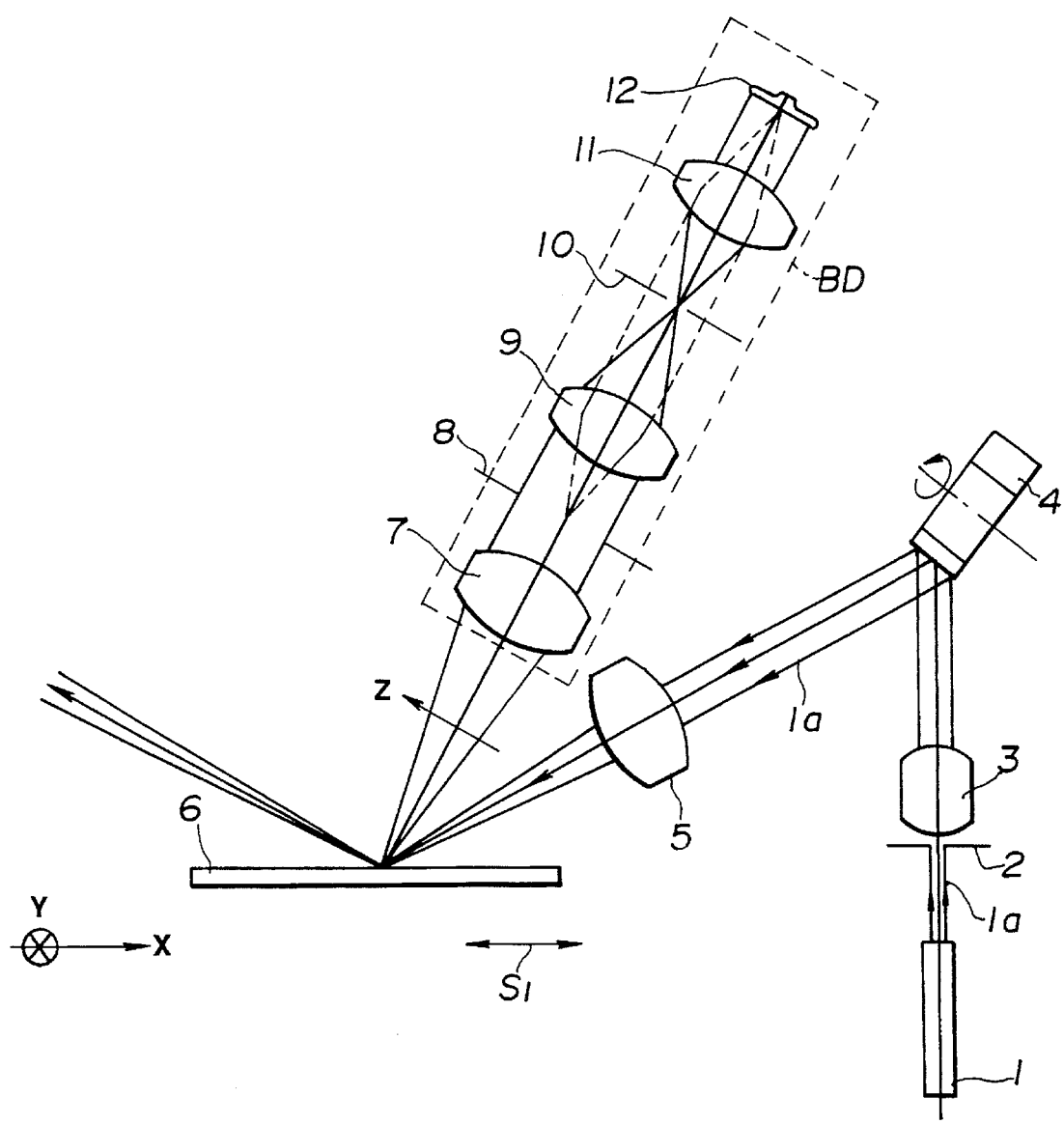
FIG. 1 is a diagram showing a foreign-matter inspection apparatus.
Figure 2:
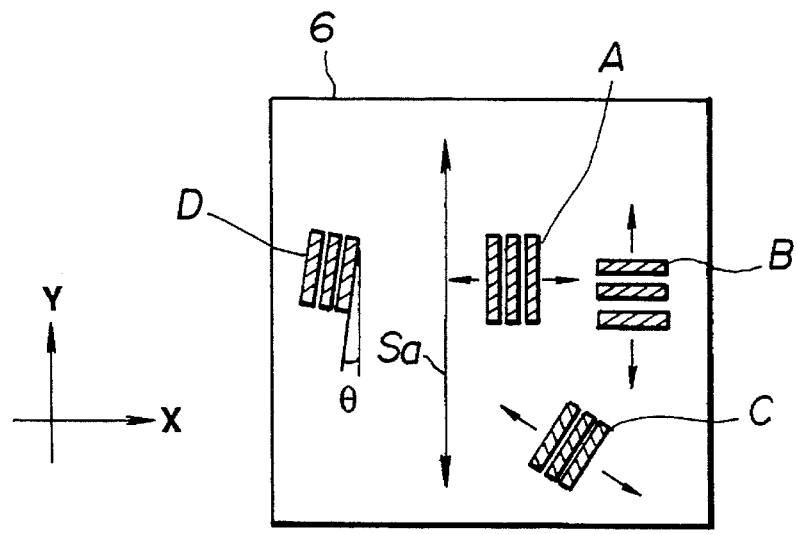
FIG. 2 is a diagram illustrating circuit patterns on a reticle.

As discussed above, FIG. 2 is a diagram illustrating circuit patterns on the surface of a reticle in an actual production process. In FIG. 2, A, B, C and D represent patterns whose directions with respect to the x axis are 90 degrees, 0 degree, 45 degrees and an arbitrary angle θ, respectively. When these patterns A, B, C and D are provided on the surface of reticle 6, and are scanned with light beam 1a in the direction of two-head arrow $S_a$, diffracted light is generated from each pattern on the surface of reticle 6. Diffracted light is incident upon detection optical system 101 and reaches photosensing unit 12 only when pattern A is subjected to optical scanning. In FIG. 7(B), $S_P$ represents pattern-diffracted light incident upon the surface of photosensing unit 12 at that time.

In the present embodiment, since light-receiving aperture 12a of photosensing unit 12 is provided to be greater than the size of the incident diffracted light beam, pattern-diffracted light SP is incident locally upon the surface of light-receiving aperture 12a. Since pattern-diffracted light $S_P$ is distributed symmetrically on the two photosensors L and R, the difference between output signals from the two photosensors L and R when using light-blocking plate 13 becomes 0. That is, it is impossible to discriminate whether the incident light is scattered light from foreign matter or pattern-diffracted light from a circuit pattern from the difference between output signals from the two photosensors L and R of photosensing unit 12.

Accordingly, in the present embodiment, light-blocking plate 13 is provided in front of photosensing unit 12 to block mainly diffracted light $S_P$ from a circuit pattern, and thereby to prevent the diffracted light $S_P$ from being incident upon photosensing unit 12.

Light-blocking plate 13 has a shape of a belt extending in the z direction so as to transmit scattered light $S_G$ from foreign matter as much as possible, and to block most of pattern-diffracted light $S_P$. Thus, in the present embodiment, the S/N ratio (the ratio of the intensity of scattered light from foreign matter to the intensity of pattern-diffracted light) is increased, and accuracy in inspection of foreign matter is thereby improved.

When reticle 6 produces an angular error (θ error) caused by deviation from a predetermined position by an angle θ, or pupil alignment between the light-projecting and light-receiving optical systems is insufficient, pattern-diffracted light $S_P$ from a portion surrounding the scanning line laterally deviates, as shown in FIG. 7(C). In such a case, pattern-diffracted light $S_P$ cannot be blocked by light-blocking plate 13, and is incident upon photosensing unit 12 (photosensor L in the case of FIG. 7(C)).

Accordingly, in the present embodiment, signals from the two photosensors L and R are processed by signal processing system 102 to discriminate scattered light from foreign matter from the above-described diffracted light from a circuit pattern.

Figure 8:
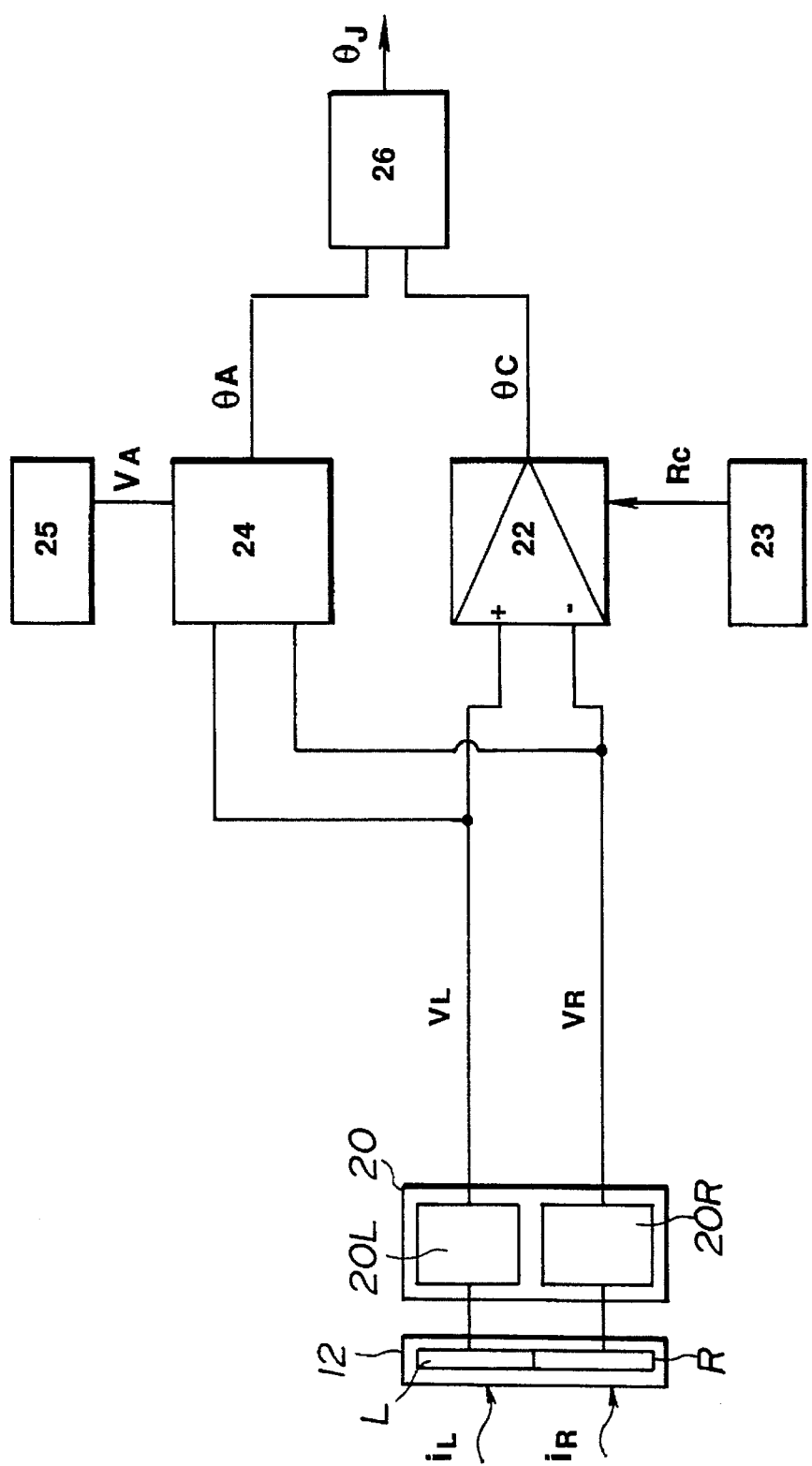
FIG. 8 is a block diagram showing signal processing system 102 of the apparatus shown in FIG. 6.

Next, a description will be provided of signal processing system 102 of the present embodiment. FIG. 8 is a block diagram of a principal portion of signal processing system 102 of the present embodiment.

In FIG. 8, pattern-diffracted light or scattered light ($i_L$, $i_R$) from a reticle incident upon respective regions (photosensors L and R) on the surface of photosensing unit 12 produces respective electrical signals, which are amplified by amplifier 20 (20L and 20R) and are output as amplified voltages ($V_L$, $V_R$), respectively. These electrical signals $V_L$ and $V_R$ are branched and input to adder 24 and comparator 22. Adder 24 electrically obtains a value ($V_L+V_R$), which is compared with a preset voltage value Va from reference-signal generator 25. If ($V_L+V_R$) ≧ $V_A$, adder 24 outputs a High level as signal $θ_A$.

On the other hand, comparator 22 obtains a value |($V_L-V_R$)/($V_L+V_R$)|, which is compared with a constant value $R_C$ obtained from reference-signal generator 23.

In the case of a completely uniform scattering distribution, $R_C$=0, since $V_L$=$V_R$.

Actually, however, since a certain amount of asymmetry is allowed in consideration of the characteristics of the sensitivity of photosensing unit 12, the optical system and the like, a value close to 0 between 0<$R_C$<1 is set. If |($V_L-V_R$)/($V_L+V_R$)|≦$R_C$, comparator 22 outputs a High level as signal $θ_C$.

Determination circuit 26 obtains the logical product ($θ_A$ ⊗ $θ_C$)$θ_J$ of signal $θ_A$ from adder 24 and signal $θ_C$ from comparator 22, and discriminates foreign matter from the circuit pattern with reference to FIG. 9.

FIG. 9 illustrates output signals from respective components (amplifiers 20L and 20R, adder 24, comparator 22 and determination circuit 26) in respective states, such as the presence of foreign matter and the presence of a circuit pattern on the surface of reticle 6, and the like, and determination methods.

A state in which output signal $θ_A$ or $θ_C$ is High is represented by 1, and a state in which output signal $θ_A$ or $θ_C$ is Low is represented by 0. Output signals $V_L$ and $V_R$ from amplifiers 20L and 20R, respectively, equal 0 when no foreign matter is present on the surface of reticle 6, and equal $V_0$ when foreign matter is present. "Circuit pattern 1 (2)" indicates a state in which only an output signal from photosensor R(L) is present. As shown in FIG. 9, it is determined that foreign matter is present on the surface of reticle 6 when the logical product $θ_J$ equals 1.

As described above, in the present embodiment, the presence of foreign matter on the surface of reticle 6 is detected while discriminating the foreign particle from a circuit pattern utilizing an output signal from determination circuit 26.

Figures 10A, 10B, 10C:
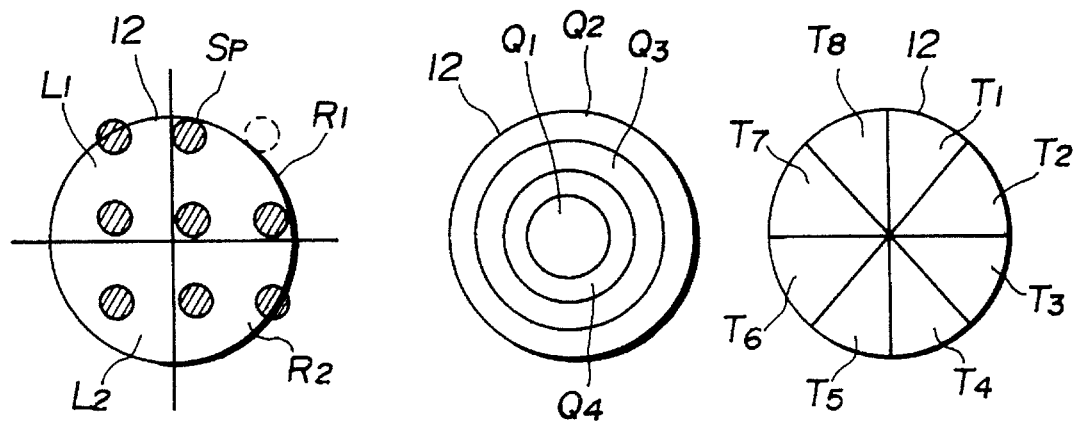
FIGS. 10(A)–10(C) are diagrams illustrating modified examples of photosensing unit 12 of the apparatus shown in FIG. 6.

Although in the present embodiment, two fractional sensors arranged symmetrically with respect to the incident cross section are used for photosensing unit 12, four fractional photosensors ($L_1$ $L_2$, $R_1$, $R_2$) shown in FIG. 10(A), a plurality of fractional concentric photosensors ($Q_1$, $Q_2$, $Q_3$, $Q_4$) shown in FIG. 10(B), a plurality of fractional radial photosensors ($T_{1-T8}$) shown in FIG. 10(C), and the like may also be used. In FIG. 10(A), $S_P$ represents a diffraction pattern generated by a contact-hole string.

In FIG. 6, light beam 1a is obliquely incident upon the surface of reticle 6, and the detection optical system is disposed so as to collect back-scattered light. However, the detection optical system may be disposed at any region where directly-advancing light (regularly-reflected light)

does not reach. For example, the light beam may be incident perpendicularly onto the surface of the reticle, and the detection optical system may be obliquely disposed, or the positions of the light beam and the detection optical system may be replaced with each other. In addition, in FIG. 6, the detection optical system may be disposed so as to collect front-scattered light.

In the present embodiment, by providing the detection optical system at a portion where directly-advancing light does not reach, the amount of pattern-diffracted light is reduced, whereby the diameter of the light beam can be increased. It is thereby possible to increase the speed of movement of the reticle, and to greatly shorten the inspection time.

Figure 11:
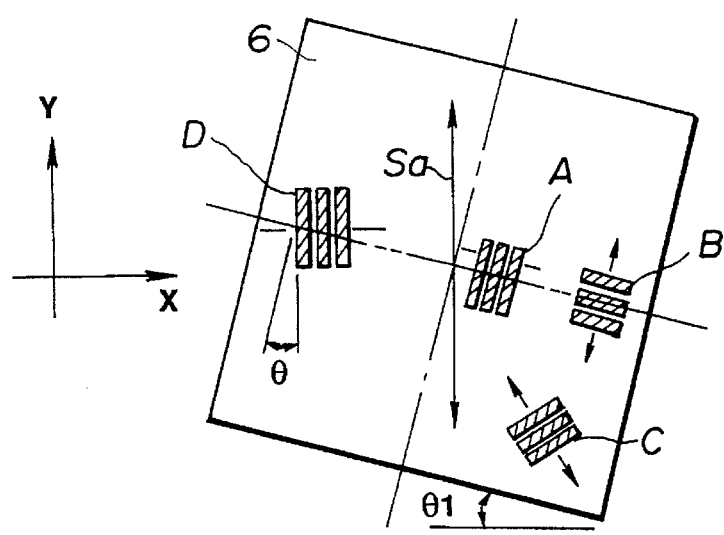
FIG. 11 is a diagram showing another example of circuit patterns on a reticle for the purpose of illustrating a second embodiment of the present invention.

FIG. 11 is a diagram showing the schematic configuration of circuit patterns on the surface of reticle 6 in a second embodiment of the present invention. The apparatus used in the present embodiment is the same as that shown in FIG. 6. The apparatus of the present embodiment is also used while being mounted in a projection exposure apparatus for device production, or independently.

The present embodiment differs from the first embodiment shown in FIG. 6 in that reticle 6 is relatively rotated by $\theta_1$ degrees within the horizontal plane. The other configuration is the same as that of the first embodiment. In the present embodiment, diffracted light beams from circuit patterns A, B and C on the surface of reticle 6 are not incident upon detection optical system 101.

However, when, for example, the angle $\theta$ of circuit pattern D equals ($\theta=$) 15 degrees, and the angular error $\theta_1$ of reticle 6 equals ($\theta_1=$) 15 degrees, diffracted light from circuit pattern D is in some cases incident upon detection optical system 101. At that time, a distribution $S_P'$ of pattern-diffracted light as shown in FIG. 12 is formed on the surface of photosensing unit 12.

Figure 12:
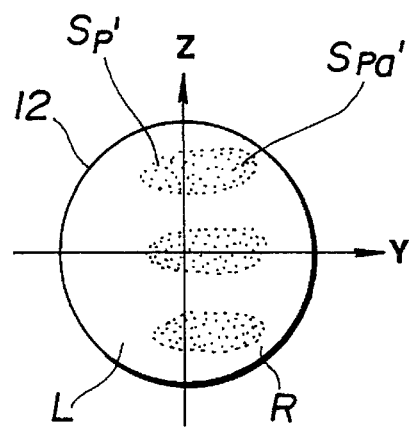
FIG. 12 is a diagram illustrating a distribution of diffracted light from pattern D shown in FIG. 11 on photosensing unit 12.

In FIG. 12, pattern-diffracted light is situated at the center of the beam scanning, and distribution $S_P'$ of diffracted light is almost symmetric with respect to the z axis if no angular error is present in the reticle. Actually, however, the distribution deviates from symmetry because of various reasons.

Figure 13:
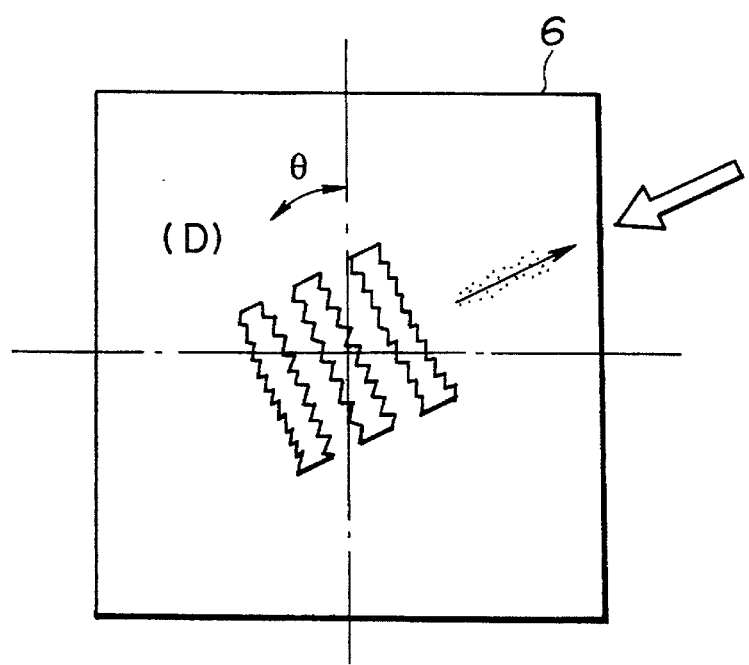
FIG. 13 is an explanatory diagram illustrating the actual structure of pattern D and diffracted light from pattern D.

In an actual production process, patterns on reticle 6 are mostly drawn using an electron beam. The patterns are formed by scanning the surface of reticle 6 with a rectangular electron beam having a size of 0.2 μm×0.2 μm–0.5 μm×0.5 μm two-dimensionally in two directions orthogonal to each other. Hence, in the case of pattern D, other than patterns A and B, fine digital errors remain at the edges of circuit pattern D, as shown in FIG. 13. If an inspection light beam indicated by the block arrow is projected onto the pattern, diffracted light caused by the pattern is not necessarily generated within the incident cross section (diffracted light $S_{Pa}'$ shown in FIG. 12).

However, by using signal processing system 102 shown in FIG. 8, a foreign particle can be discriminated from the circuit pattern in the above-described manner, and the presence of foreign matter on the surface of the reticle 6 can be detected with high accuracy.

As in the first embodiment shown in FIG. 6, in the present embodiment, light-blocking plate 13 may or may not be provided in front of photosensing unit 12.

Figure 14:
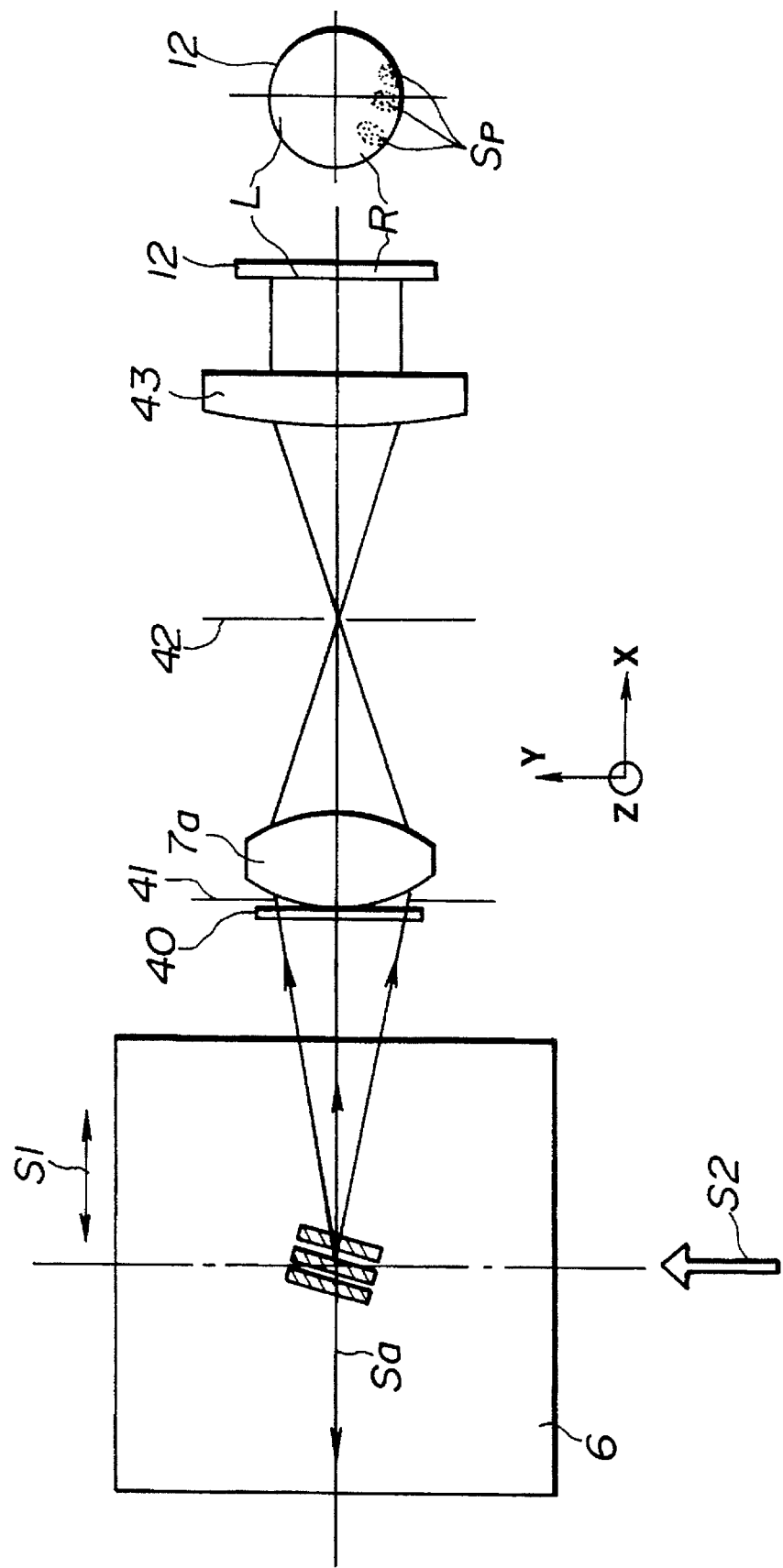
FIG. 14 is a diagram showing the schematic configuration of a foreign-matter inspection apparatus according to a third embodiment of the present invention.
Figure 15:
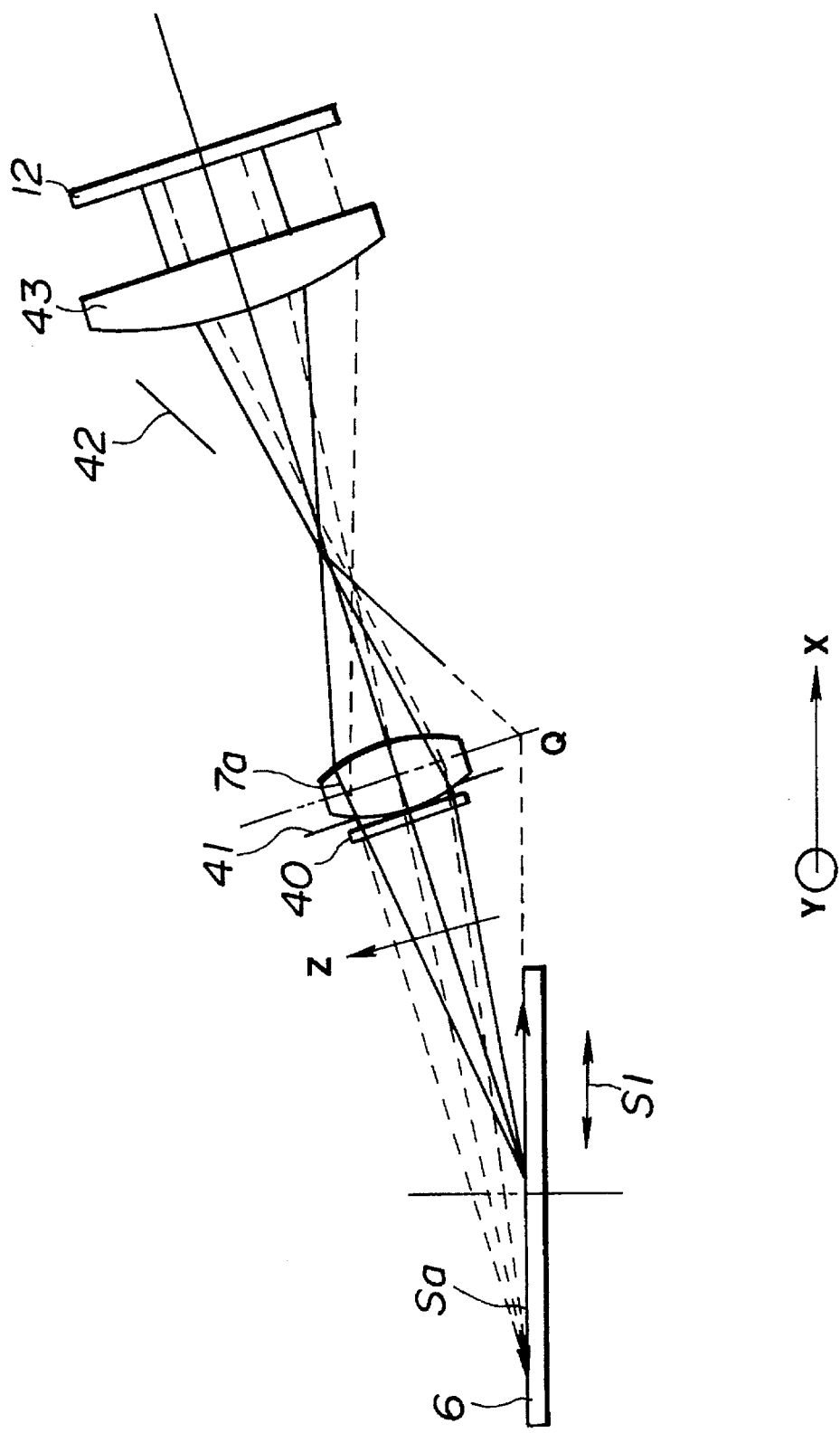
FIG. 15 is an explanatory diagram illustrating the configuration of an x-z cross section of the apparatus shown in FIG. 14.

FIG. 14 is a diagram showing the schematic configuration of a portion of an apparatus according to a third embodiment of the present invention. FIG. 15 is an explanatory diagram showing an x-z cross section of the apparatus shown in FIG. 14. The apparatus of the present embodiment is also used while being mounted in a projection exposure apparatus for device production, or independently.

The present embodiment differs from the first embodiment shown in FIG. 6 in that a polarized light beam is projected onto the surface of reticle 6, and scattered light having a predetermined polarized state from the surface of reticle 6 is detected by detection optical system 101. In addition, a portion of detection optical system 101 slightly differs. The other configuration is substantially the same as the configuration of the first embodiment.

In the present embodiment, the surface of reticle 6 is subjected to optical scanning in the direction of arrow $S_a$ with an S-polarized light beam from below, as indicated by block arrow $S_2$. Laterally-scattered light produced from reticle 6 is condensed by light-receiving lens 7a via polarizing filter 40 for passing P-polarized light and aperture stop 41.

Light-receiving lens 7a images scanning line $S_a$ onto the plane of field stop 42 while satisfying so-called Sheimflug's conditions. The light beam passing through field stop 42 is guided to photosensing unit 12, comprising fractional sensors, by condensor lens 43. Aperture stop 41 is substantially conjugate to photosensing unit 12 via light-receiving lens 7a and condenser lens 43. The presence of foreign matter on the surface of reticle 6 is detected utilizing a signal from photosensing unit 12.

Also in the present embodiment, pattern-diffracted light is in some cases asymmetrically distributed on the light receiving surface of photosensing unit 12 depending on the directional property of a circuit pattern on the surface of reticle 6. Even in such a case, by using the signal processing system 102 shown in FIG. 8, foreign matter can be discriminated from the circuit pattern in the same manner as described above, whereby foreign matter on the surface of the reticle is detected with high accuracy.

Figure 16:
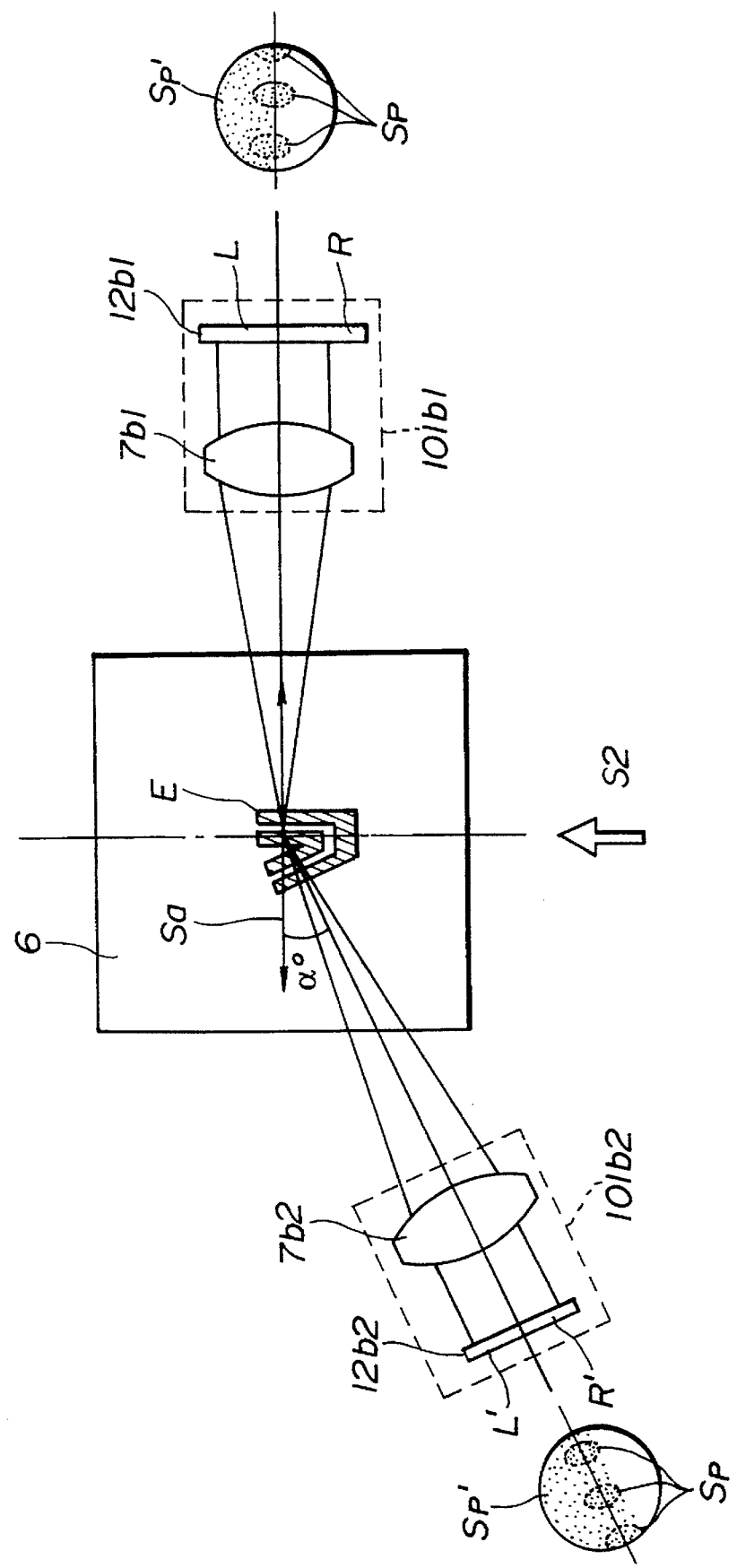
FIG. 16 is a diagram showing the schematic configuration of a foreign-matter inspection apparatus according to a fourth embodiment of the present invention.

FIG. 16 is a diagram showing the schematic configuration of a principal portion of an apparatus according to a fourth embodiment of the present invention. The apparatus of the present embodiment is also used while being mounted in a projection exposure apparatus for device production, or independently.

In the present embodiment, the surface of reticle 6 is scanned while projecting a light beam from below in the direction indicated by block arrow $S_2$ to form scanning line $S_a$. Scattered light from foreign matter and diffracted light from the circuit pattern on the surface of reticle 6 are sensed from two entirely different directions by detection optical systems 101b1 and 101b2.

Detection optical systems 101b1 and 101b2 include light-receiving lenses 7b1 and 7b2, and photosensing units 12b1 and 12b2, each comprising two photosensors L and R, and L' and R', respectively. The positions of photosensing units 12b1 and 12b2 correspond to the position of aperture stop 8 shown in FIG. 6.

In a conventional surface-condition inspection apparatus, it is assumed that scattered light from foreign matter is uniformly directed in all directions, while diffracted light from a circuit pattern has anisotropy (directivity) and therefore is directed only in one direction. Hence, signals obtained from two detection systems, each comprising a single photosensor, are compared with each other to discriminate the foreign matter from the circuit pattern.

In such a conventional surface-condition inspection apparatus, however, as shown in FIG. 16, if circuit patterns having a plurality of directivities are provided within the diameter of a light beam, the two detection systems simultaneously detect the diffracted light to erroneously detect foreign matter.

Accordingly, it is preferable to configure at least one of the detection optical systems 101b1 and 101b2 by a plurality of fractional photosensors. In the present embodiment, each of the two detection optical systems 101b1 and 101b2 is configured by fractional photosensors.

The distribution of diffracted light from a composite pattern E having a plurality of directivities is not necessarily symmetric with respect to the light-receiving optical axis. Hence, an asymmetric distribution of pattern-diffracted light is obtained on the light receiving surface of the photosensing unit. In FIG. 16, each of patterns $S_P$ and $S_P'$ represents diffracted light from such a pattern.

In the present embodiment, foreign matter is discriminated from a circuit pattern using the above-described signal processing system by utilizing the distribution of diffracted light at that time. Scattered light from foreign matter is not necessarily generated uniformly in two entirely different directions. According to the present embodiment, even in the case of foreign matter having anisotropy, if scattered light is incident upon one of the detection optical systems, uniformity in the distribution of diffracted light on the light receiving surface of the photosensing unit of that detection optical system is sufficiently higher than that of pattern-diffracted light. Hence, the presence of foreign matter can be detected with high accuracy.

The present invention also may be applied to a reticle or a mask having a pellicle, serving as a surface to be inspected, for preventing dust particles, as well as the surface of a reticle (glass surface).

Although the above-described plurality of fractional photosensors or independent sensors which constitute a photosensing unit are disposed symmetrically with respect to the light-receiving optical axis, they are not necessarily symmetrically disposed. The present invention may be applied to any other configuration of fractional sensors provided that they are configured so that the difference between outputs from the sensors can be obtained most effectively for a specific pattern.

The individual components shown in outline or designated by blocks in the drawings are all well-known in the surface-condition inspection method and apparatus arts and their specific construction and operation are not critical to the operation or best mode for carrying out the invention.

While the present invention has been described with respect to what is presently considered to be the preferred embodiments, it is to be understood that the invention is not limited to the disclosed embodiments. To the contrary, the present invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method for inspecting surface conditions of an object, on which a pattern is formed, by detecting scattered light generated by the surface of the object using a detection optical system, said method comprising the steps of:

illuminating the surface of the object;

providing first and second photodetectors substantially on a pupil plane of the detection optical system for detecting scattered light from the surface of the object, the pupil plane of the detection optical system being positioned off an optical path of regularly reflected light and an optical path of directly advancing light generated when the object is illuminated in said illuminating step;

generating a first signal corresponding to the sum of outputs of the first and second photodetectors, and a second signal corresponding to the difference between the outputs of the first and second photodetectors; and comparing the first signal with a first threshold value and the second signal with a second threshold value, and obtaining the logical product of the result of the comparisons for inspecting surface conditions of the object.

2. A method according to claim 1, further comprising dividing the difference between the outputs of the first and second photodetectors by the sum of the outputs of the first and second photodetectors to generate the second signal.

3. A method according to claim 1, further comprising representing the comparison of the first signal with the first threshold value by 1 when the first signal is not less than the first threshold value, and by 0 when the first signal is less than the first threshold value, and representing the comparison of the second signal with the second threshold value by 1 when the second signal is equal to or less than the second threshold value, and by 0 when the second signal is greater than the second threshold value.

4. An apparatus for detecting surface conditions of an object on which a pattern is formed, said apparatus comprising:

means for illuminating the object;

a detection optical system for detecting scattered light generated by the object illuminated by said illuminating means, said detection optical system having a pupilar plane at a position off an optical path of regularly reflected light and an optical path of directly-advancing light generated when illuminating the object;

first and second photodetectors provided at the pupilar plane of said detection optical system for detecting scattered light from the surface of the object;

comparison means for comparing a signal corresponding to the sum of the outputs of said first and second photodetectors with a first threshold value, and for comparing a signal corresponding to the difference between the outputs of said first and second photodetectors with a second threshold value; and means for detecting a logical product of the results of the comparison by said comparison means.

5. An apparatus according to claim 4, further comprising means for producing the signal corresponding to the difference between the outputs of said first and second photodetectors by dividing the difference between the outputs of said first and second photodetectors by the sum of the outputs of said first and second photodetectors.

6. An apparatus according to claim 4, wherein said detection optical system comprises a member for blocking diffracted light generated by the pattern.

7. An apparatus according to claim 4, wherein the object comprises one of a reticle and a mask on which a circuit pattern is formed.

8. An apparatus according to claim 4, wherein said illuminating means comprises optical scanning means for moving a light beam on the object.

9. An apparatus according to claim 4, wherein said detection optical system comprises an aperture stop for defining said pupil plane and said first and second photodetectors are provided at one of a plane of said aperture stop and a conjugate image thereof.

10. An apparatus according to claim 9, wherein said first and second photodetectors are provided symmetrically with respect ot a plane including an optical axis of said detection optical system and orthogonal to the surface to be inspected.

11. A device manufacturing method comprising the steps of:

providing a mask having a pattern to be printed;

inspecting surface conditions of the mask; and exposing the mask to print the pattern onto a substrate, wherein said inspecting step comprises:

illuminating the surface of the mask;

providing first and second photodetectors substantially on a pupil plane of a detection optical system for detecting scattered light from the surface of the mask, the pupil plane of the detection optical system being positioned off an optical path of regularly-reflected light and an optical path of directly-advancing light generated when the mask is illuminated in said illuminating step;

generating a first signal corresponding to the sum of outputs of the first and second photodetectors, and a second signal corresponding to the difference between the outputs of the first and second photodetectors; and comparing the first signal with a first threshold value and the second signal with a second threshold value, and obtaining the logical product of the result of the comparisons for inspecting surface conditions of the mask.

12. An exposure apparatus comprising:

inspecting means for inspecting surface conditions of a mask having a pattern to be printed; and exposing means for exposing the mask to print the pattern onto a substrate, wherein said inspecting means comprises:

means for illuminating the mask;

a detection optical system for detecting scattered light generated by the mask illuminated by said illuminating means, said detection optical system having a pupilar plane at a position off an optical path of regularly reflected light and an optical path of directly-advancing light generated when illuminating the object;

first and second photodetectors provided at the pupilar plane of said detection optical system for detecting scattered light from the surface of the mask;

comparison means for comparing a signal corresponding to the sum of the outputs of said first and second photodetectors with a first threshold value, and for comparing a signal corresponding to the difference between the outputs of said first and second photodetectors with a second threshold value; and means for detecting a logical product of the results of the comparison by said comparison means.

13. A method for inspecting foreign matter on a surface of an object, on which a pattern is formed, by detecting scattered light generated from the surface of the object using a detection optical system, said method comprising the steps of:

illuminating the surface of the object;

providing first and second photodetectors substantially on a pupil plane of the detection optical system for detecting scattered light from the surface of the object, the pupil plane of the detection optical system being positioned off an optical path of regularly reflected light and an optical path of directly advancing light generated when the object is illuminated in said illuminating step;

generating a first signal corresponding to the sum of outputs of the first and second photodetectors, and a second signal corresponding to the difference between the outputs of the first and second photodetectors; and distinguishing the foreign matter from the pattern on the surface of the object, on the basis of the first and second signals.

14. A method according to claims 13, wherein said illuminating step comprises illuminating one of a reticle and a mask on which a circuit pattern is formed.

15. A method according to claim 13, wherein said illuminating step comprises scanning a light beam on the object.

* * * * *